United States Patent [19]
Dinsdale

[11] Patent Number: 5,733,307
[45] Date of Patent: Mar. 31, 1998

[54] BONE ANCHOR HAVING A SUTURE TROUGH

[75] Inventor: Michael C. Dinsdale, Richardson, Tex.

[73] Assignee: AMEI Technologies, Inc., Wilmington, Del.

[21] Appl. No.: 710,406

[22] Filed: Sep. 17, 1996

[51] Int. Cl.$^6$ ............................................. A61B 17/04
[52] U.S. Cl. .................................. 606/232; 606/104
[58] Field of Search ............................. 606/232, 104

[56] References Cited

U.S. PATENT DOCUMENTS

| | | | |
|---|---|---|---|
| 4,507,817 | 4/1985 | Staffeld | 7/158 |
| 4,537,185 | 8/1985 | Stednitz | 128/92 B |
| 4,632,100 | 12/1986 | Somers et al. | 128/92 |
| 4,738,255 | 4/1988 | Goble et al. | 128/92 YF |
| 4,976,715 | 12/1990 | Bays et al. | 606/77 |
| 5,019,079 | 5/1991 | Ross | 606/72 |
| 5,037,422 | 8/1991 | Hayhurst et al. | 606/72 |
| 5,047,030 | 9/1991 | Draenert | 606/65 |
| 5,100,417 | 3/1992 | Cerier et al. | 606/232 |
| 5,156,616 | 10/1992 | Meadows et al. | 606/232 |
| 5,176,682 | 1/1993 | Chow | 606/232 |
| 5,268,001 | 12/1993 | Nicholson et al. | 606/72 |
| 5,364,400 | 11/1994 | Rego, Jr. et al. | 606/72 |
| 5,403,136 | 4/1995 | Mathys | 411/310 |
| 5,417,533 | 5/1995 | Lasner | 411/426 |
| 5,464,427 | 11/1995 | Curtis et al. | 606/232 |
| 5,522,843 | 6/1996 | Zang | 606/232 |

OTHER PUBLICATIONS

PCT, International Patent Application No. PCT/US91/07003, Abstract, International Publication Date: 2 Apr. 1992, 1 page.

International Search Report, International Application No. PCT/US93/01186, dated Jul. 21, 1993.

Supplemental European Search Report, European Patent Application No. 93905855.8, dated Nov. 16, 1994.

*Primary Examiner*—Gary Jackson
*Attorney, Agent, or Firm*—Baker & Botts, L.L.P.

[57] ABSTRACT

A bone anchor with a suture trough for attaching bone to tissue using a suture. The bone anchor includes a threaded bone anchor body having a major diameter, a minor diameter, a tip, and a drive head. A suture trough is formed within the anchor body with a width greater than or equal to the diameter of the suture and a depth below the minor diameter greater than or equal to the diameter of the suture. A suture passageway connects the opposing portions of the suture trough. The suture seats within the suture trough during insertion of the bone anchor into the bone.

35 Claims, 2 Drawing Sheets

BONE ANCHOR HAVING A SUTURE TROUGH

TECHNICAL FIELD OF THE INVENTION

The present invention relates generally to medical devices and more particularly to a bone anchor having an external suture trough for use in connecting soft tissue to bone.

BACKGROUND OF THE INVENTION

Modern medical techniques include suturing soft tissue to bone, for example, during reconstructive surgery. In one form, this technique involves attaching the suture to a bone anchor, inserting the bone anchor into the bone, and connecting the tissue to the bone via the suture. The bone anchor allows the surgeon to connect soft tissue to bone using a suture.

Conventional bone anchors attach the suture to the bone anchor in ways that limit the bone anchor's effectiveness in practice. The Odgen and Statak bone anchors are examples of currently used anchors. Both the Ogden and Statak have threaded anchor bodies. The Odgen anchor requires a special tool to route the suture though center axis hole of the anchor and the drive tool. The suture must be knotted at the lead end of the anchor to prevent pull out through the center hole and keep the suture stationary in the anchor. The requirement of knotting the suture in the Ogden anchor limits its use to a "non-slip" mode of operation. The Statak anchor requires routing the suture through an eyelet at the drive end of the anchor. While the eyelet allows a "slip mode" of operation, the eyelet is also used as the drive to insert the Statak anchor into bone. The Statak eyelet can be susceptible to mechanical failure (twisting off) due to its relatively small cross-sectional area. Needles cannot be pre-attached to the suture in either the Odgen or Statak bone anchors due to the lack of center axis hole clearance in the bone anchor and/or associated driver.

SUMMARY OF THE INVENTION

The present invention provides a bone anchor having a suture trough that substantially eliminates or reduces disadvantages and problems associated with previously developed bone anchor systems and methods.

More specifically, the present invention provides an improved bone anchor that includes a threaded bone anchor body having a major diameter, a minor diameter, a tip, and a drive head. A suture trough is formed within the anchor body having a width greater than or equal to the diameter of the suture and a depth below the minor diameter greater than or equal to the diameter of the suture. A suture passageway connects the opposing portions of the suture trough. The suture seats within the suture trough during insertion of the bone anchor into the bone.

The present invention provides an important technical advantage by providing a trough in the anchor in which the suture resides during insertion of the bone anchor into the bone. This allows the use of the bone anchor in either non-slip (knotted suture) or slip (unknotted suture) mode.

The present invention provides another important technical advantage because it does not require a special suture threading tool.

The present invention provides another important technical advantage because needles can be attached to the suture prior to inserting the bone anchor into the bone.

The present invention provides another important technical advantage because the suture's holding strength is the suture line break strength rather than the pullout tension of the suture knot.

The present invention provides another important technical advantage by eliminating or greatly reducing mechanical failure of the anchor. The suture trough allows the present invention to use a drive socket, rather than a drive end (such as the one used on the Statak bone anchor), to provide a bone anchor that is less susceptible to mechanical failure during insertion.

The present invention provides another important technical advantage by providing a relatively non-abrasive surface against which the suture acts when tensioned, to reduce the likelihood of suture breakage.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the Figures like numerals being used to refer to like and corresponding parts of the various drawings.

In one embodiment, the present invention provides a bone anchor with an exterior suture trough for securing suture to bone when reattaching soft tissue. The suture trough provides the means for easily loading suture line into the bone anchor without requiring a special suture threading tool. Suture can be secured to the bone anchor with or without needles attached. The suture trough feature of the present invention allows the suture to be used in either a "slip" or "non-slip" mode. "Slip mode" allows suture to slide back and forth through the bone anchor, while "non-slip mode" holds the suture stationary in the bone anchor. When the suture is knotted for "non-slip" mode, the knot can be positioned in an eyelet or counter bored hole to hold the suture stationary in the bone anchor. These features allow a surgeon either mode of operation using a single type of bone anchor.

Figure 1:
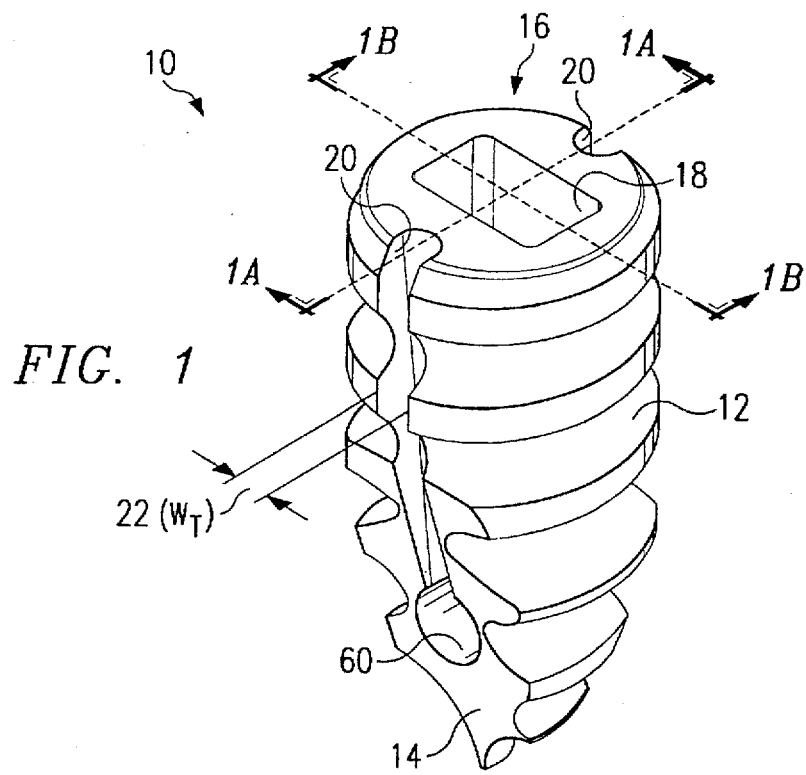
FIG. 1 shows an isometric view of one embodiment of the present invention with a self-drilling tip.

FIG. 1 is an isometric view of a self-drilling embodiment of the bone anchor 10 of the present invention. Bone anchor 10 includes bone anchor body 12 having a drive head 16 and a tip 14. Bone anchor 10 is preferably manufactured from titanium. Tip 14 shown in FIG. 1 is a spade drill tip 14 that provides a self-drilling feature to the bone anchor 10 by allowing the bone anchor to directly drill into the bone without first tapping the bone. A drive pocket 18 is countersunk into the head 16 of bone anchor 10 to provide a means to drive bone anchor 10 in or out of bone. The drive pocket 18 shown in FIG. 1 is a rectangular pocket for receiving a rectangular drive. It should be understood that drive pocket 18 can assume other shapes to conform to a variety of drives for screwing the bone anchor 10 into and out of the bone.

Figure 1A:
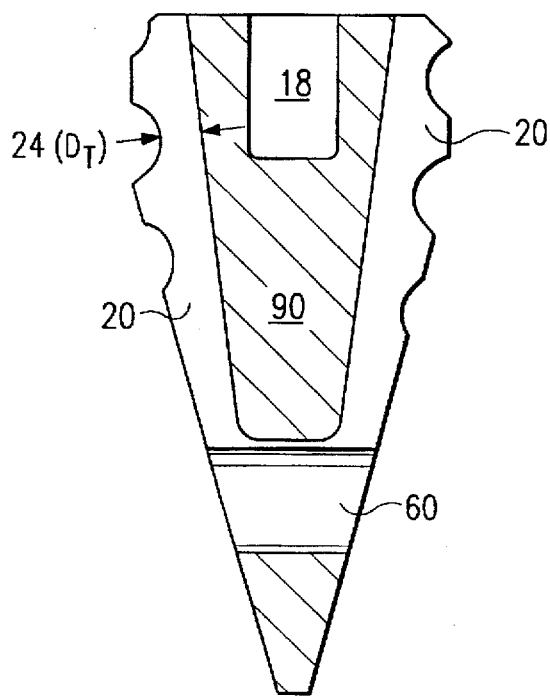
FIG. 1A shows a sectional view of the embodiment of FIG. 1 along section line 1A.
Figure 1B:
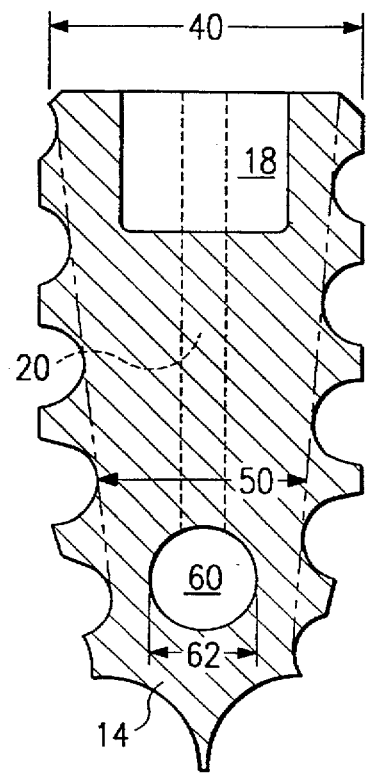
FIG. 1B shows a sectional view of the embodiment of FIG. 1 along section line 1B.

As shown in FIG. 1B, the threaded anchor body 12 has a major screw diameter 40 and a minor screw diameter 50. The major diameter 40 remains constant, while minor diameter 50 increases, or "runs out", from the tip 14 to the head 16 of bone anchor 10. The run out provides a larger cross sectional area at the head 16 of the bone anchor 10 to provide a larger cross section drive pocket 18 for relatively small bone anchors 10. A larger cross section enhances the strength of the drive pocket 18 to decrease the likelihood of mechanical failure during insertion of the bone anchor 12. In an alternative embodiment, the anchor body 12 could be made wide enough that a run out would not be necessary to provide a mechanically sound drive pocket 18.

Suture trough 20 is a trough formed in anchor body 12 that runs on opposing sides of the anchor body 12. In the embodiment shown in FIG. 1, suture trough 20 runs approximately parallel to the minor thread diameter 50. Suture trough 20 is recessed below minor thread diameter 50 by a depth 24 ($D_T$), shown in FIG. 1A. Suture trough 20 has a width 22 ($W_T$), shown in FIG. 1. Both the width and depth of suture trough 20 should be greater than or equal to the diameter of the suture to be used with the bone anchor 10. This allows the suture to seat within the suture trough 20 such that the suture remains below minor diameter 50 to prevent contact between the suture and the bone when bone anchor 10 is screwed into the bone. Suture that remains within the suture trough 20 will not suffer damage due to contact with bone during insertion of the bone anchor 10 into the bone.

As shown in FIG. 1, the opposing portions of suture trough 20 connect through passageway 60. In the embodiment of FIG. 1, passageway 60 is a circular eyelet cross-drilled into tip 14. The diameter of the eyelet 60 will preferably exceed the width 22 of suture trough 20 to provide an area for a suture knot to reside during "non-slip" operation. Suture is loaded onto bone anchor 12 by routing the suture through cross-drilled eyelet 60 and pulling the suture taut to seat the suture in suture trough 20 from tip 14 to drive head 16 on either side of bone anchor 10.

Figure 2:
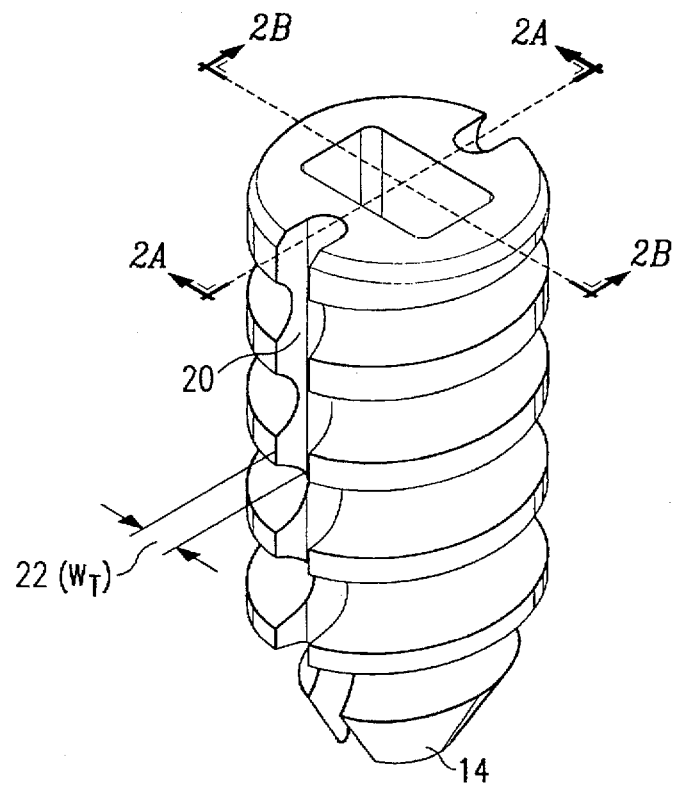
FIG. 2 shows an isometric view of another embodiment of the present invention with a self-tapping tip.
Figure 2A:
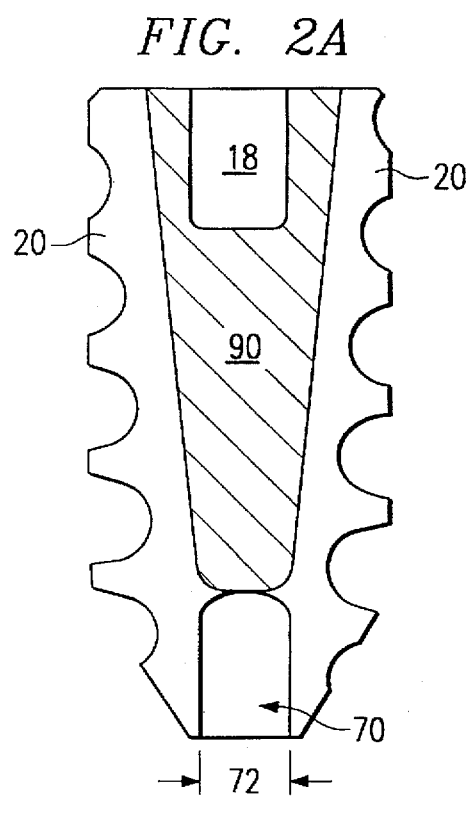
FIG. 2A shows a sectional view of the embodiment of FIG. 2 along section line 2A.
Figure 2B:
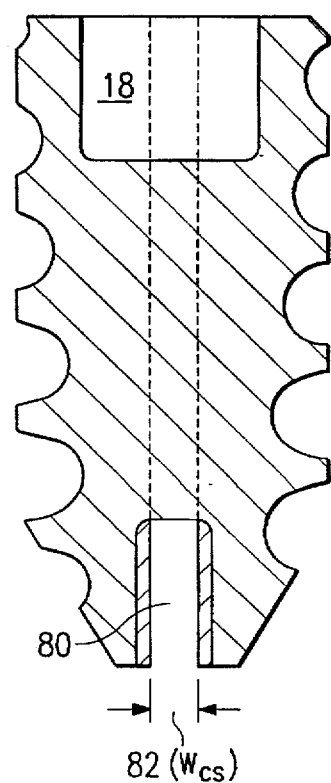
FIG. 2B shows a sectional view of the embodiment of FIG. 2 along section line 2B.

FIG. 2 is an isometric illustration of a self tapping embodiment of bone anchor 10. FIGS. 2A and 2B show sectional views of the embodiment of FIG. 2. The self-tapping bone anchor 10 requires drilling a pilot hole into the bone prior to screwing the bone anchor 10 into the bone. The embodiment of FIG. 2 has a non-tapered or straight, threaded anchor body 12 with a beveled tip 14. Bevelled tip 14 includes a passageway 60 that includes counter bore 70 along the center axis of the anchor 10 and a cross slot 80. The counter bore 70 preferably has a diameter that exceeds the width of the suture trough 20 and provides the area for holding a knot in a knotted suture. Cross slot 80 provides the passageway that connects the opposing portions of suture trough 20. Cross slot 80 will have a width 82 ($W_{CS}$) approximately equal to the width of the suture trough 20 ($W_T$). Major diameter 40, minor diameter 50, minor diameter runout, drive head 16, and drive pocket 18, suture trough width, and suture trough depth are as described in FIGS. 1, 1A and 1B.

In operation of the present invention, suture line is sent through passageway 60 and pulled taut to seat the suture in the suture trough 20. For an eyelet style passageway 60, the suture would be threaded through the eyelet, whereas for a counter bore-type passageway 60, the suture could be layed into or pulled through. The suture can attach to a drive tool to pull the suture taut, thereby seating the suture in the suture trough 20 and securing the bone anchor 10 to the drive tool. The suture line can pass through the passageway 60 either with or without a needle attached, depending on the need of the specific operation. The drive tool can then rotate to screw the bone anchor 10 and suture into the bone. The suture trough 20 of the present invention allows the suture to remain below the minor diameter 50 when driving bone anchor 12 into bone to avoid suture line damage. The suture trough 20 and passageway 60 configuration of the present invention provide an advantage over conventional bone anchors by allowing a surgeon to attach a needle to the suture prior to inserting the bone anchor 10. This option provides a potential advantage because the surgeon does not have to attach the needle to the suture after the bone anchor is screwed into the bone, and in close proximity to both the bone and the soft tissue.

The present invention provides another advantage by allowing both "slip" and "non-slip" modes of operation using the same bone anchor 10. In "non-slip" mode, a knot is tied in the suture prior to seating the suture in suture trough 20. The knot is tied so that an appropriate amount of suture extends on either side of the knot. The knot is then lodged within the passageway 60 (lodged within the eyelet of FIG. 1 or the counter bore 70 of FIG. 2) and the suture seats in suture trough 20 and cross slot 80 of FIG. 2). The eyelet diameter 62 and the counter bore 70 width 72 should both exceed the width of the suture trough so that the knot will enter the eyelet, but will not pass into the suture trough 20. The bone anchor 10 can then be screwed into the bone. The bone surrounds the passageway 60 of bone anchor 10 to help hold the knot within the passageway 60. The surgeon can then attach the suture opposite the knot to the soft tissue and pull the soft tissue to the bone. Because the suture is a single piece with a knot tied in it, and not two separate pieces of suture tied together to form the knot, the failure strength is the suture line break strength rather than the pull out strength of the knot.

In "slip" mode, the suture is seated in the suture trough 20 without a knot in the suture line. A surgeon can then screw the bone anchor 10 into the bone, attach one end of the suture to the soft tissue, pull the suture to the anchor, thereby pulling the soft tissue to the bone, and tie off the suture. The suture trough 20 of the present invention provides a slot through which the suture can "slip" to allow the suture to be pulled through the suture trough after the bone anchor 10 has been inserted into the bone. Some conventional bone anchors, such as the Ogden bone anchor, do not provide the surgeon the slip mode option because the Ogden bone anchor requires a knotted, fixed suture. The slip mode of operation provides another potential advantage by allowing the surgeon to pull through potentially damaged suture without having to remove the bone anchor. For example, if the suture were to be damaged at a place within the bone after the bone anchor 10 was installed, the suture could be slipped through the suture trough 20 to expose the damaged portion, cut to remove the damages portion, and used in the operation without having to remove the bone anchor.

The drive pocket 18 of the present invention provides a larger cross sectional area to use to drive the anchor into the bone than some conventional bone anchors. The Statak bone anchor, for example, has a relatively thin, rectangular drive end with a circular hole through which the suture is threaded. The relatively thin drive end is subject to mechanical failure (twisting off) during insertion into the bone and can provide a relatively sharp edge contacting the suture that could lead to cutting or damaging the suture. In contrast, the present invention provides a female-type drive pocket with a larger cross sectional area for driving the bone anchor into the bone. Furthermore, the present invention provides a smoother contact surface with a larger cross sectional area 90 between the bone anchor and the suture to reduce the likelihood of cutting the suture during operation.

In summary, the present invention provides a bone anchor with a suture trough for use in attaching bone to tissue. The bone anchor includes a threaded bone anchor body having a major diameter, a minor diameter, a tip, and a drive head. A suture trough is formed within the anchor body having a width greater than or equal to the diameter of the suture and a depth below the minor diameter greater than or equal to the diameter of the suture. A suture passageway connects the opposing portions of the suture trough. The suture seats within the suture trough during insertion of the bone anchor into the bone to reduce or eliminate damage to the suture. The present invention allows needles to be attached to the suture prior to insertion of the bone anchor into the bone, allows both slip and non-slip modes of operation, and provides an increased cross sectional area for driving the anchor into the bone to reduce or eliminate mechanical failures of the bone anchor.

Although the present invention has been described in detail, it should be understood that various changes, substitutions and alterations can be made hereto without departing from the spirit and scope of the invention as described by the appended claims. For example, another embodiment of the present invention could comprise a self-tapping anchor similar to the embodiment of FIG. 2, but replacing the cross slot and counter bore with an eyelet as in FIG. 1 (but without the spade drill tip shown in FIG. 1).

What is claimed is:

1. A bone anchor for insertion into bone together with a suture, comprising:
   a bone anchor body, said bone anchor body having a driver end and a lead-in end, said bone anchor body having a threaded surface formed by broken threads such that said threaded surface has at least one suture trough extending longitudinally along said bone anchor body; and
   a tip at said lead-in end, said tip having a suture eyelet that is substantially perpendicular to the longitudinal axis of said anchor body;
   wherein said suture trough and said suture eyelet are of sufficient dimensions so as to completely contain said suture such that said bone anchor may be inserted into said bone without frictional contact between said bone and said suture.

2. The bone anchor of claim 1, wherein said at least one suture trough is formed on the exterior of said bone anchor body, extending from the drive end to said tip.

3. The bone anchor of claim 1, wherein the depth of the suture trough is approximately equal to the width of the suture trough.

4. The bone anchor of claim 1, wherein the bone anchor further comprises a drive pocket formed in said drive end, said drive pocket operable to receive a drive for inserting the bone anchor into bone.

5. The bone anchor of claim 1, wherein the eyelet is circular.

6. The bone anchor of claim 1, wherein the anchor body is tapered such that said drive end has a cross sectional area larger than that of said lead-in end.

7. The bone anchor of claim 6, wherein the anchor body has a major diameter defined by the outer edges of said threads and a minor diameter defined by the bases of said threads and wherein said major diameter and minor diameter are substantially parallel to each other.

8. The bone anchor of claim 6, wherein the anchor body has a major diameter defined by the outer edges of said threads and a minor diameter defined by the bases of said threads and wherein said major diameter and said minor diameter diverge with respect to each other.

9. The bone anchor of claim 1, where the anchor body has a cross sectional area that is substantially constant along said longitudinal axis.

10. The bone anchor of claim 9, wherein the anchor body has a major diameter defined by the outer edges of said threads and a minor diameter defined by the bases of said threads and wherein said major diameter and said minor diameter are substantially parallel to each other.

11. The bone anchor of claim 9, wherein the anchor body has a major diameter defined by the outer edges of said threads and a minor diameter defined by the bases of said threads and wherein said major diameter and said minor diameter diverge with respect to each other.

12. The system of claim 1, wherein the tip comprises a spade drill tip to form a self-drilling bone anchor.

13. The system of claim 1, wherein the tip comprises a counter bored bevel tip for use with a pilot hole in the bone.

14. The bone anchor of claim 1, wherein said threaded surface has a pair of said suture troughs and wherein said suture eyelet connects said suture troughs.

15. The bone anchor of claim 14, wherein said suture troughs are on opposing sides of said bone anchor body.

16. A method for attaching suture to bone using a bone anchor, comprising:
   forming a threaded bone anchor body with a minor diameter and a major diameter;
   forming a suture trough on opposing sides of the bone anchor body such that the suture trough has a width greater than or equal to the diameter of the suture and a depth below the minor diameter greater than or equal to the diameter of the suture;
   forming a tip in the bone anchor body;
   forming a drive head in the bone anchor body;
   forming a suture passageway in the tip of the bone anchor body to connect the opposing portions of the suture trough;
   attaching a suture to the bone anchor;
   seating the suture within the suture trough;
   inserting the bone anchor into the bone.

17. The method of claim 16, wherein attaching suture to the bone anchor further comprises sending the suture through the suture passageway such that the suture can slip through the suture passageway and the suture trough after the bone anchor has been inserted into the bone.

18. The method of claim 16, wherein attaching suture to the bone anchor further comprises knotting the suture and lodging the knot within the suture passageway to hold the suture stationary within the bone anchor.

19. The method of claim 16 further comprising;
   attaching a needle to the suture prior to attaching the suture to the bone anchor.

20. The method of claim 16, further comprising;
   attaching the suture to a drive tool, thereby securing the bone anchor to the drive tool; and
   rotating the drive tool to insert the bone anchor into the bone.

21. A bone anchor for insertion into bone together with a suture, comprising:
- a bone anchor body, said bone anchor body having a driver attachment end and a lead-in end, said bone anchor body having a threaded surface formed by broken threads such that said broken threaded surface has at least one suture trough extending longitudinally along said bone anchor body; and
- a tip at said lead-in end, said tip having a suture cross slot that is substantially perpendicular to the longitudinal axis of said anchor body and that has sufficient dimensions such that such suture may be at least partially contained within said cross slot;
- wherein said at least one suture trough is of sufficient dimensions so as to completely contain said suture such that said bone anchor may be inserted into said bone without frictional contact between said bone and said suture.

22. The bone anchor of claim 21, wherein said tip has a cavity adjacent said cross slot, said cavity having dimensions sufficient to contain at least a portion of a knot of said suture.

23. The bone anchor of claim 22, wherein said cavity is a counter bore substantially perpendicular to said cross slot.

24. The bone anchor of claim 21, wherein said cross slot has dimensions sufficient so as to completely contain said suture such that said suture does not contact said bone at said tip when said anchor is inserted into said bone.

25. The bone anchor of claim 21, wherein said at least one suture trough is formed on the exterior of said bone anchor body, extending from the drive end to said tip.

26. The bone anchor of claim 21, wherein the depth of the suture trough is approximately equal to the width of the suture trough.

27. The bone anchor of claim 21, wherein the bone anchor further comprises a drive pocket formed in said drive end, said drive pocket operable to receive a drive for inserting the bone anchor into bone.

28. The bone anchor of claim 21, wherein the anchor body is tapered such that said drive end has a cross sectional area larger than that of said lead-in end.

29. The bone anchor of claim 28, wherein the anchor body has a major diameter defined by the outer edges of said threads and a minor diameter defined by the bases of said threads and wherein said major diameter and minor diameter are substantially parallel to each other.

30. The bone anchor of claim 21, where the anchor body has a cross sectional area that is substantially constant along said longitudinal axis.

31. The bone anchor of claim 30, wherein the anchor body has a major diameter defined by the outer edges of said threads and a minor diameter defined by the bases of said threads and wherein said major diameter and said minor diameter are substantially parallel to each other.

32. The bone anchor of claim 30, wherein the anchor body has a major diameter defined by the outer edges of said threads and a minor diameter defined by the bases of said threads and wherein said major diameter and said minor diameter diverge with respect to each other.

33. The bone anchor of claim 30, wherein the anchor body has a major diameter defined by the outer edges of said threads and a minor diameter defined by the bases of said threads and wherein said major diameter and said minor diameter diverge with respect to each other.

34. The bone anchor of claim 21, wherein said thread surface has a pair of suture troughs and wherein said cross slot connects said suture troughs.

35. The bone anchor of claim 28, wherein said suture troughs are on opposing sides of said bone anchor body.

* * * * *